(12) United States Patent
Riou et al.

(10) Patent No.: US 6,342,487 B1
(45) Date of Patent: Jan. 29, 2002

(54) COMPOSITIONS CONTAINING AT LEAST ONE FARNESYL TRANSFERASE INHIBITOR AND AT LEAST ONE TOPOISOMERASE INHIBITOR AND COMPOSITIONS CONTAINING AT LEAST ONE FARNESYL TRANSFERASE INHIBITOR AND AT LEAST ONE TAXOID

(75) Inventors: Jean-François Riou, Paris; Patrick Mailliet, Fontenay Sous Bois; Patricia Vrignaud, Combs la Ville, all of (FR)

(73) Assignee: Aventis Pharma Rorer S.A., Antony (FR)

( * ) Notice: Subject to any disclaimer, the term of this patent is extended or adjusted under 35 U.S.C. 154(b) by 0 days.

(21) Appl. No.: 09/346,296

(22) Filed: Jul. 2, 1999

(30) Foreign Application Priority Data

Dec. 21, 1998 (FR) .............................. 98 16125

(51) Int. Cl.$^7$ ..................... A01N 43/50; A01N 43/60; A61K 31/40; A61K 43/02
(52) U.S. Cl. ..................... 514/80; 514/280; 514/410; 514/449; 514/922
(58) Field of Search ..................... 514/80, 280, 449, 514/410, 922

(56) References Cited

U.S. PATENT DOCUMENTS

| 5,645,988 A | | 7/1997 | Woude et al. ................. 435/6 |
| 6,013,662 A | * | 1/2000 | Bourzat et al. ............. 514/410 |
| 6,096,757 A | * | 8/2000 | Bishop et al. .............. 514/290 |

FOREIGN PATENT DOCUMENTS

| WO | WO 98/54966 | * 12/1998 | ................. 514/356 |

OTHER PUBLICATIONS

Vrignaud, P. et al., "In Vivo Combination of RPR 130401, a Non–Peptidomimetic Farnesyltransferase Inhibitor, with Chemotherapy," *American Association for Cancer Research*, vol. 40, No. 3453, pp. 523–524 (1999).

* cited by examiner

*Primary Examiner*—Frederick Krass
(74) *Attorney, Agent, or Firm*—Finnegan, Henderson, Farabow, Garrett & Dunner, L.L.P.

(57) ABSTRACT

Combinations containing at least one farnesyl transferase inhibitor and at least one topoisomerase inhibitor. Combinations containing at least one taxoid and at least one farnesyl transferase inhibitor.

11 Claims, No Drawings

COMPOSITIONS CONTAINING AT LEAST ONE FARNESYL TRANSFERASE INHIBITOR AND AT LEAST ONE TOPOISOMERASE INHIBITOR AND COMPOSITIONS CONTAINING AT LEAST ONE FARNESYL TRANSFERASE INHIBITOR AND AT LEAST ONE TAXOID

The present invention relates to compositions comprising at least one farnesyl transferase inhibitor compound and at least one topoisomerase inhibitor. The present invention also relates to compositions comprising at least one farnesyl transferase inhibitor together with at least one taxoid.

The protein farnesyl transferase is an enzyme which catalyses the transfer of the farnesyl group from farnesyl pyrophosphate (FPP) to the terminal cysteine residue of the CAAX tetrapeptide sequence of a certain number of proteins and, in particular, of the p21 Ras protein expressing the ras oncogene. The ras oncogene (H—, N— or K-ras) is known to play a key role in the routes of cell communication and the processes of cell division. The mutation of the ras oncogene or its overexpression is often associated with human cancer: the mutated p21Ras protein is found in numerous human cancers and especially in more than 50% of cancers of the colon and 90% of cancers of the pancreas (Kohl et al., Science, 260, 1834–1837, 1993). The inhibition of farnesyl transferase and consequently of farnesylation of the p21Ras protein blocks the capacity of the mutated p21Ras protein to induce cell proliferation and to transform normal cells into cancerous cells.

On the other hand, it has been demonstrated that the inhibitors of farnesyl transferase are likewise active on tumor cell lines not expressing mutated or overexpressed ras, but having the mutation of an oncogene or the overexpression of an oncoprotein whose route of communication uses the farnesylation of a protein, such as a normal ras (Nagasu et al., Cancer Research 55, 5310–5314, 1995; Sepp-Lorenzino et al., Cancer Research 55, 5302–5309, 1995).

The inhibitors of the farnesyl transferase protein are inhibitors of cell proliferation and consequently anti-tumor and anti-leukemic agents. In particular, the compounds described in U.S. application Ser. No. 08/999,408, filed on Dec. 29, 1997, now U.S. Pat. No. 6,013,662 the disclosure of which is specifically incorporated herein by reference, and the international application WO 98/29390, the disclosure of which is specifically incorporated herein by reference, are inhibitors of farnesyl transferase of very particular interest.

The topoisomerases are well-known enzymes which control the topology of the DNA in the course of replication, transcription and recombination. Two large classes of topoisomerases are known: the topoisomerases of type I, monomeric enzymes, catalyzing the opening/closing of a single strand of DNA; the topoisomerases of type II, multimeric enzymes, catalyzing these reactions on the two strands of DNA. Topoisomerases of type III are likewise known. See, e.g., Slichenmeyer et al. J Natl Cancer Inst 1993; 85: 271–291; Potmesil, Cancer Research 1994; 54: 1431–1439; Duguet et al., Medicine/Sciences 1994: 10: 962–972, Wall et al., J Am Chem Soc 1966; 88: 3888–3890, Gottlieb et al., Cancer Chemother Rep 1970; 54: 461–470, and Hsiang et al., Cancer Res 1988; 48: 1722–1726.

The topoisomerase inhibitors act by stabilization of the cleavage complex formed by the enzyme attached to the strand of DNA. This leads to the production of irreversible cleavages of the DNA, triggering a cell apoptosis program.

Among the topoisomerase I inhibitors, it is especially possible to mention camptothecin and its derivatives; in particular topotecan and irinotecan (CPT-II). Among the topoisomerase II inhibitors, it is possible to mention epipodophyllotoxin derivatives such as etoposide and the anthracyclines.

Taxoids are anticancer agents suitable for administration to a patient in need thereof. Examples of taxoids include TAXOTERE® illustrated below:

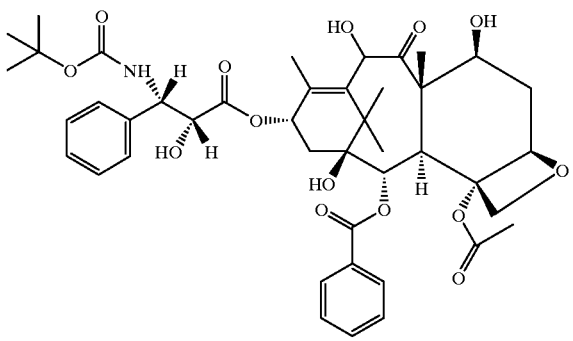

TAXOTERE® is disclosed, for example, in U.S. Pat. Nos. 5,670,536 and 4,814,470, the disclosures of which are specifically incorporated by reference herein. Another taxoid example is:

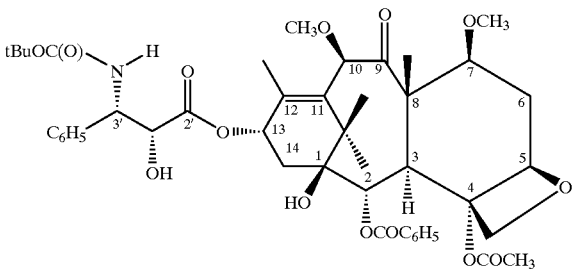

i.e., 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate disclosed in U.S. Pat. No. 5,847,170, the disclosure of which is specifically incorporated by reference herein. Additional taxoids include TAXOL®, as disclosed in U.S. Pat. No. 5,254,580, at column 1, lines 21–33, which column 1 disclosure is specifically incorporated herein by reference, and 4α-10β-diacetoxy-2α-benzoyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate disclosed in U.S. Pat. No. 5,587,493, the disclosure of which is specifically incorporated herein by reference. Taxoids have been found to be therapeutically useful in anticancer treatments.

A subject of the present invention is improvement of the efficacy of farnesyl transferase inhibitor compounds when administered in combination with at least one topoisomerase inhibitor or when administered in combination with at least one taxoid. Within the meaning of the invention, "combination" is understood as including the association, including physical association, of, e.g., the at least one farnesyl transferase inhibitor compound and at least one topoisomerase inhibitor in which the compounds are present in separate form and can be administered separately, as well as situations where the molecules are not present in separate form in the combination.

Combination within the meaning of the invention is further defined as optionally including, in addition to:
(1) at least one farnesyl transferase inhibitor compound and at least one topoisomerase inhibitor and
(2) at least one taxoid with at least one farnesyl transferase inhibitor, at least one other substance therapeutically useful in the treatment of neoplastic diseases, chosen from:
    the alkylating agents such as cyclophosphamide, ifosfamide, melphalan, hexamethylmelamine, thiotepa or dacarbazine,
    antimetabolites such as pyridmine analogs such as 5-fluorouracil and cytarabine or its analogs such as 2-fluorodeoxycytidine or folic acid analogs such as methotrexate, idatrexate or trimetrexate,
    spindle poisons including vinca alkaloids such as vinblastine or vincristine or their synthetic analogs such as navelbine, or estramustine or taxoids,
    epipodophyllotoxins (a class of topoisomerase inhibitors), such as etoposide or teniposide,
    antibiotics such as daunorubicin, doxorubicin, bleomycin or mitomycin,
    enzymes such as L-asparaginase,
    pyridobenzoindole derivatives and
    various agents such as procarbazine, mitoxantrone, platinum coordination complexes such as cisplatin or carboplatin, biological response modifiers or growth factor inhibitors such as interferons or interleukins, or else growth factors of hematopoietic type such as G-CSF or GM-CSF, or radiotherapy.

A subject of the invention relates to the combinations comprising at least one farnesyl transferase inhibitor compound and at least one topoisomerase inhibitor; preferentially the combinations comprising a farnesyl transferase inhibitor with a topoisomerase inhibitor I inhibitor; the present invention also includes combinations comprising at least one farnesyl transferase inhibitor compound and at least one topoisomerase II inhibitor.

Another subject of the invention relates to the combinations comprising at least one taxoid and at least one farnesyl transferase inhibitor. In particular, the present invention relates to the combinations comprising at least one farnesyl transferase inhibitor and at least one taxoid, preferably chosen from TAXOL®, TAXOTERE®, and the other specific taxoids disclosed above.

A preferred aspect of the invention utilizes at least one farnesyl transferase inhibitor compound chosen from those described in U.S. application Ser. No. 08/999,408, filed on Dec. 29, 1997, now U.S. Pat. No. 6,013,662 the disclosure of which is specifically incorporated herein by reference, and the international application WO 98/29390, the disclosure of which is specifically incorporated herein by reference, of general formula (I):

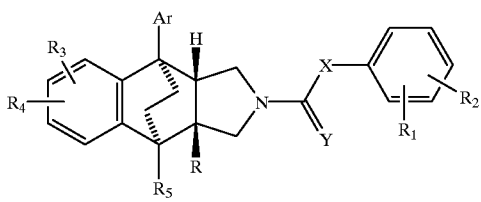

(I)

in which:
Ar is
    a phenyl radical substituted by one or more identical or different atoms or radicals, chosen from halogen atoms and alkyl radicals containing 1 to 4 carbon atoms, such as methyl, alkenyl containing 2 to 4 carbon atoms, hydroxyl, mercapto, alkylthio, alkylsulfonyl or alkylsulfinyl, amino, alkylamino or dialkylamino, formyl, alkylcarbonyl, carboxyl, alkoxycarbonyl, carbamoyl, alkylcarbamoyl or dialkylcarbamoyl, cyano or trifluoromethyl, alkoxy containing 1 to 4 carbon atoms, such as methoxy, whose alkyl portion is possibly perhalogenated, such as trifluoromethoxy, or
    a phenyl radical fused to a heterocycle of 4 to 7 chain members containing one or more heteroatoms chosen from oxygen, nitrogen and sulfur atoms, it especially being possible for the bicyclic system thus formed to be chosen from 2,3-dihydro-1,4-benzodioxin-6-yl or 2,3-dihydrobenzofuran-5-yl or 2,3-dihydrobenzopyran-6-yl radicals or
    a polycyclic aromatic radical, such as 1- or 2-naphthyl or 5-indanyl, or 1,2,3,4-tetrahydronaphth-6-yl
    a heterocyclic aromatic radical of 5 to 12 chain members incorporating one or more heteroatoms chosen from oxygen, nitrogen and sulfur atoms, which is linked to the fused ring by a carbon-carbon bond, said radical being substituted, if necessary, by one or more identical or different atoms or radicals, chosen from halogen atoms and alkyl and alkenyl radicals containing 2 to 4 carbon atoms, hydroxyl, alkoxy radicals containing 1 to 4 carbon atoms, mercapto, alkylthio, alkylsulfonyl or alkylsulfinyl, amino, alkylamino or dialkylamino, formyl, alkylcarbonyl, carboxyl, alkoxycarbonyl, carbamoyl, alkylcarbamoyl or dialkylcarbamoyl, cyano or trifluoromethyl radicals, preferentially, Ar is a 2,3-dihydro-1,4-benzodioxin-6-yl or 2,3-dihydrobenzofuran-5-yl radical, or a phenyl radical substituted in position 4, preferably by a methyl, trifluoromethyl or methoxy radical; in particular, the 2,3-dihydro-1,4-benzodioxin-6-yl radical; very advantageously, Ar is a phenyl radical substituted in position 4 by a methyl radical, with, for all of these radicals, alkyl containing 1 to 4 carbon atoms, R is
a radical of general formula

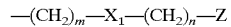

in which
X$_1$ is a single bond or an oxygen or sulfur atom,
m is a whole number equal to 0 or 1,
n is a whole number equal to 0, 1 or 2,
one or more methylene radicals can be substituted by a carboxyl, alkoxycarbonyl, carbamoyl, alkylcarbamoyl, dialkylcarbamoyl, amino, alkylamino or dialkylamino radical with, for all of these radicals, alkyl containing 1 to 4 carbon atoms,
Z is
a carboxyl radical,
a COOR$_6$ radical, in which R$_6$ is a linear alkyl radical containing 1 to 3 carbon atoms, such as methyl, or a branched alkyl radical containing 3 carbon atoms
a radical of formula CON(R$_7$)(R$_8$) in which
    R$_7$ is a hydrogen atom or a linear alkyl radical containing 1 to 6 carbon atoms or a branched alkyl radical containing 3 to 6 carbon atoms and $R_8$ is
- a hydrogen atom,
- a hydroxyl radical,
- an arylsulfonyl radical, such as phenylsulfonyl, optionally substituted by one or more identical or different atoms or radicals, chosen from halogen atoms and alkyl and alkoxy radicals, with, for these radicals, alkyl containing 1 to 4 carbon atoms,
- a heterocycle of 5 to 7 chain members incorporating one or more heteroatoms chosen from nitrogen, oxygen or sulfur atoms, it being possible for said heterocycle to be linked by a heteroatom,
- an amino radical optionally substituted by one or two identical or different radicals chosen from the radicals
  - alkyl containing 1 to 4 carbon atoms,
  - aryl, such as phenyl, optionally substituted by one or more identical or different radicals, chosen from alkyl and alkoxy radicals with, for these radicals, alkyl containing 1 to 4 carbon atoms,
  - heterocyclyl of 5 to 7 chain members and containing one or more heteroatoms chosen from nitrogen, oxygen and sulfur atoms,
  - arylcarbonyl, such as benzoyl, optionally substituted by one or more identical or different radicals, chosen from alkyl and alkoxy radicals with, for these radicals, alkyl containing 1 to 4 carbon atoms,
- an alkoxy radical containing 1 to 6 carbon atoms in a linear chain or 3 to 6 carbon atoms in a branched chain, either chain being optionally substituted by a phenyl radical,
- a linear alkyl radical containing 1 to 6 carbon atoms, such as methyl, or a branched alkyl radical containing 3 to 6 carbon atoms, either being optionally substituted by an amino, alkylamino, dialkylamino or hydroxyl radical, an alkoxy radical containing 1 to 4 carbon atoms, a mercapto, alkylthio, alkoxycarbonyl, carboxyl, cyano, a mono- or polycyclic aromatic radical having 5 to 12 chain members, incorporating or not incorporating one or more heteroatoms chosen from oxygen, nitrogen and optionally substituted sulfur atoms, it being possible for said aromatic radical to be, especially, the 2- or 3- or 4-pyridyl radical, preferentially 3-pyridyl or 4-pyridyl, or pyridine N-oxide, or it also being possible for it to be a phenyl radical optionally substituted by one or more halogen atoms or by one or more hydroxyl, amino or trifluoromethyl groups, or by one or more C2 to C4 alkyl or alkenyl, alkoxy, alkylthio, alkylamino, alkylcarbonyl or alkoxycarbonyl radicals, a carbamoyl, alkylcarbamoyl or dialkylcarbamoyl whose alkyl part is C1 to C8, formyl or else a 1- or 2-naphthyl radical or, preferentially, R is a carboxyl radical, or a —COOMe radical, or else a —CON($R_7$)($R_8$) radical for which, when $R_7$ is a hydrogen atom, $R_8$ is a methyl radical substituted by the 3-pyridyl radical;

very advantageously, R is a carboxyl radical;

of very particular interest, R is a —CON($R_7$)($R_8$) radical for which, when $R_7$ is a hydrogen atom, $R_8$ is a methyl radical substituted by the 3-pyridyl radical;

Z is
- a PO(OR$_9$)$_2$ radical in which $R_9$ is a hydrogen atom or a linear alkyl radical containing 1 to 6 carbon atoms or a branched alkyl radical containing 3 to 6 carbon atoms or
- an —NH—CO—T radical in which T is a hydrogen atom or a linear alkyl radical containing 1 to 6 carbon atoms or a branched alkyl radical containing 3 to 6 carbon atoms, either being optionally substituted by an amino, carboxyl, alkoxycarbonyl, hydroxyl, alkoxy, mercapto or alkylthio radical, or else -a-CH$_2$—$^+$N⟨pyridinium⟩ radical having, as counterion, an anion, such as trifluoromethanesulfonate, with, for all of the radicals having an alkyl group which are proposed in the definition of Z, alkyl containing 1 to 4 carbon atoms.

$R_1$ and $R_2$, which are identical or different, are a hydrogen atom, a halogen or an alkyl radical, an alkoxy radical, such as methoxy, each optionally substituted by a dialkylamino radical of which each alkyl part contains 1 to 4 carbon atoms or forms, with the nitrogen atom, a saturated heterocycle containing 5 or 6 chain members, an alkylthio radical, an alkoxycarbonyl radical, or else when situated ortho with respect to one another, $R_1$ and $R_2$ can form a saturated or unsaturated heterocycle containing 1 or 2 heteroatoms chosen from nitrogen and oxygen, optionally substituted by a halogen atom or by an alkyl or alkoxy radical, preferentially, one of the symbols $R_1$ or $R_2$ is a hydrogen atom and the other of the symbols is a methoxy radical, and more advantageously attached in the ortho position of the phenyl ring, with, for all of the radicals having an alkyl group which are proposed in the definition of $R_1$ and $R_2$, alkyl containing 1 to 4 carbon atoms.

$R_3$ and $R_4$, which are identical or different, are a hydrogen or halogen atom or an alkyl, hydroxyl, alkoxy, alkylcarbonyloxy, mercapto, alkylthio, alkylsulfonyl or alkylsulfinyl, amino, alkylamino or dialkylamino, alkoxycarbonylamino, carboxyl, alkoxycarbonyl, carbamoyl, alkylcarbamoyl or dialkylcarbamoyl, formyl, alkylcarbonyl, cyano or trifluoromethyl radical, preferentially, or else $R_3$ and $R_4$ are each a hydrogen atom, or else one of the symbols $R_3$ or $R_4$ is a hydrogen atom and the other of the symbols $R_3$ or $R_4$ is a methoxy radical, and more advantageously in position 5 of the benzoperhydroisoindole nucleus;

very advantageously, $R_3$ and $R_4$ are each a hydrogen atom;

with, for all of the radicals having an alkyl group which are proposed in the definition of $R_3$ and $R_4$, alkyl containing 1 to 4 carbon atoms;

$R_5$ represents a hydrogen atom or an alkyl radical, an alkylthio radical, with, for the definition of $R_5$, alkyl containing 1 to 4 carbon atoms;

preferentially, $R_1$ is a hydrogen atom or a methyl radical;

very advantageously, $R_5$ is a hydrogen atom;

X is an oxygen or sulfur atom or an —NH—, —CO—, methylene, alkene-1-diyl group such as vinyldiyl or cycloalkane-1,1-diyl containing 3 to 6 carbon atoms, preferentially, X is a methylene or vinyldiyl group,
particularly advantageously, X is the vinyldiyl group, and
Y is an oxygen or sulfur atom,
preferentially, Y is an oxygen atom,
in racemic form or in the form of optical isomers, preferably the dextrorotatory enantiomer, as well as in the form of the salts of the product of general formula (I).
Advantageously according to the present invention, farnesyl transferase inhibitor compounds which can be mentioned are the compounds of general formula (I) for which:
Ar is a 2,3-dihydro-1,4-benzodioxin-6-yl or 2,3-dihydrobenzofuran-5-yl radical, or a phenyl radical substituted in position 4, preferably by a methyl, trifluoromethyl or methoxy radical,
R is a carboxyl radical, or a —COOMe radical, or else a —CON($R_7$)($R_8$) radical for which, when $R_7$ is a hydrogen atom, $R_8$ is a methyl radical substituted by the 3-pyridyl radical,
one of the symbols $R_1$ or $R_2$ is a hydrogen atom and the other of the symbols is a methoxy radical, and more advantageously attached in the ortho position of the phenyl ring,
or else $R_3$ and $R_4$ each represent a hydrogen atom, or else one of the symbols $R_3$ or $R_4$ is a hydrogen atom and the other of the symbols $R_3$ or $R_4$ is a methoxy radical, and more advantageously in position 5 of the benzoperhydroisoindole nucleus,
$R_5$ is a hydrogen atom or a methyl radical,
X is a methylene or vinyldiyl group,
Y is an oxygen atom;
in racemic form or in the form of optical isomers, preferably the dextrorotatory enantiomer as well as in the form of salts.

Very particularly advantageously according to the present invention, preferred farnesyl transferase inhibitor compounds are the compounds of general formula (I) selected individually from:

(3aRS,4SR,9SR,9aRS)-4,9-ethano-2[2-(2-methoxyphenyl)propenoyl]-9-(4-methylphenyl)-2,3,3a,4,9,9a-hexahydro-1H-benzo[f]isoindole-3a-carboxylic acid (3aRS,4SR,9SR,9aRS)-4,9-ethano-2[2-(2-methoxyphenyl)-propenoyl]-9-(4-methylphenyl)-2,3,3a,4,9,9a-hexahydro-1H-benzo[f]isoindole-3a-N-(3-pyridylmethyl)carboxamide (3a RS,4SR,9SR,9aRS)-9-(2,3-dihydro-1,4-benzodioxin-6-yl)-4,9-ethano-2[2-(2-methoxyphenyl)propenoyl]-2,3,3a,4,9,9a-hexahydro-1H-benzo[f]isoindole-3a-[N-(3-pyridylmethyl)carboxamide (3aRS,4SR,9SR,9aRS)-4,9-ethano-2-[2-(2-methoxyphenyl)propenoyl]9-(4-trifluoromethylphenyl)-2,3,3a,4,9,9a-hexahydro-1H-benzo[f]isoindole-3a-carboxylic acid (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid (3aRS,4SR,9SR,9aRS)-4,9-ethano-2[2-(2-methoxyphenyl)-2-propenoyl]-4-methyl-9-(4-methoxyphenyl)-2,3,3a,9,9a-hexahydro-1H-benzo[f]isoindole-3a-carboxylic acid
in racemic form or in the form of optical isomers, preferably the dextrorotatory enantiomer, as well as in the form of salts.

According to a preferred aspect, the present invention relates to the combinations comprising at least one farnesyl transferase inhibitor compound described in U.S. application Ser. No. 08/999,408, filed on Dec. 29, 1997, now U.S. Pat. No. 6,013,662 the disclosure of which is specifically incorporated herein by reference, and the application WO 98/29390, the disclosure of which is specifically incorporated herein by reference, especially such as those described above, with a topoisomerase type I inhibitor. Among the topoisomerase I inhibitors, irinotecan (CPT-11) or camptothecin is preferred, and irinotecan (CPT-11) is most preferred.

In particular, it is especially possible to mention according to the invention the combinations comprising the dextrorotatory enantiomer of (3aRS,4SR,9SR,9aRS)-4,9-ethano-2[2-(2-methoxyphenyl)propenoyl]-9-(4-methylphenyl)-2,3,3a,4,9,9a-hexahydro-1H-benzo[f]isoindole-3a-carboxylic acid with camptothecin, as well as the combinations comprising the dextrorotatory enantiomer of (3aRS,4SR,9SR,9aRS)-4,9-ethano-2[2-(2-methoxyphenyl)propenoyl]-9-(4-methylphenyl)-2,3,3a,4,9,9a-hexahydro-1H-benzo[f]isoindole-3a-carboxylic acid with irinotecan.

As a result of their mechanism of action, the farnesyl transferase inhibitor compounds, especially the compounds mentioned above, in general have a cytostatic-type activity.

In employing the combinations according to the invention comprising at least one farnesyl transferase inhibitor and at least one topoisomerase inhibitor or at least one farnesyl transferase inhibitor and at least one taxoid, a goal is to obtain an increased anti-cancer activity, such as, for example, a prolonged stabilization of the size of the tumor, or a tumor regression.

A prolonged stabilization of the size of the tumor can be obtained in a statistically more significant manner.

According to the present invention, a composition is active if after its administration, it allows the growth of the tumor to be limited.

On the other hand, a particularly advantageous characteristic of the combinations according to the present invention relates to the toxicity: indeed, the combinations according to the invention can be well tolerated; in combination with the topoisomerase inhibitor, the farnesyl transferase inhibitor has been found not to increase the toxicity of the topoisomerase inhibitor; in particular, in combination with the topoisomerase inhibitor irinotecan, the farnesyl transferase inhibitor product A does not increase the toxicity of irinotecan.

The combinations according to the present invention can advantageously prolong or maintain the anticancer activity of the topoisomerase inhibitor, in comparison with the activities obtained with each of its constituents considered in isolation; thus an advantageous characteristic of the combinations according to the invention can be an increase in the delay of tumor growth.

The improved efficacy of a combination can likewise be demonstrated by a determination of therapeutic synergism.

A combination shows a therapeutic synergism if its therapeutic activity is higher than that of one or the other of the constituents when it is used at its optimal dose [T. H. CORBETT et al., Cancer Treatment Reports, 66, 1187 (1982)].

To demonstrate the efficacy of a combination, it may be necessary to compare the maximum tolerated dose of the combination at the maximum tolerated dose of each of the isolated constituents in the study considered.

This efficacy can be quantified, for example, by the net log 10 of the killed cells which is determined according to the following formula:

net log 10 of the killed cells=[T-C (days)−duration of the treatment (days)]/[3.32·Td]

in which T-C represents the delay in tumor growth which is the median time, in days, which the tumors of the treated group (T) and the tumors of the control group (C) took to reach a predetermined value (1 g for example) and Td represents the time, in days, necessary for the doubling of the volume of the tumor in the control animals [T. H. CORBETT et al., Cancer, 40, 2660–2680 (1977); F. M. SCHABEL et al., Cancer Drug Development, Part B, Methods in Cancer Research, 17, 3–51, New York, Academic Press Inc. (1979)].

A product is considered as very active if net log 10 of the killed cells is greater than or equal to 2.8. An active cytostatic product is a product which allows the growth of the tumor to be prevented during the period of the treatments. In such a case, the net log 10 of the killed cells has a positive value.

The combination, used at its own maximum tolerated dose, in which each of the constituents will be present at a dose which is generally lower than or equal to its maximum tolerated dose, will show a therapeutic synergy when the net log 10 of the killed cells is higher than the value of the net log 10 of the killed cells of the better constituent when it is administered alone.

The present invention likewise relates to pharmaceutical compositions comprising the combinations according to the invention comprising at least one farnesyl transferase inhibitor and at least one topoisomerase inhibitor. The present invention also relates to pharmaceutical compositions comprising at least one farnesyl transferase inhibitor and at least one taxoid.

The products which form the combination can be administered simultaneously, separately or sequenced over time, it being possible to adapt this frequency so as to obtain the maximum efficacy of the combination; it being possible for each administration to have a variable duration ranging from a rapid total administration to a continuous perfusion. The products which form the combination can be administered at different rates. They can be administered independently according to schemes chosen from the continuous, intermittent, repeated, alternated or sequential schemes. The administrations can be repeated a number of times per day.

Advantageously, the farnesyl transferase inhibitor having a cytostatic activity can be administered according to a continuous scheme; advantageously, this scheme allows the plasma levels to be maintained higher than or equal to the concentration necessary to inhibit 50% of the growth of the cells (IC$_{50}$) in the in-vitro test. Advantageously, the topoisomerase inhibitor or the taxoid can be administered according to a scheme dependent on the type of tumor model; preferably according to an intermittent scheme.

It results from this that, within the meaning of the present invention, the combinations are not uniquely limited to those which are obtained by physical association of the constituents, but also to those which allow a separate administration which can be simultaneous or spread out over time; in particular, the constituents can be administered independently according to distinct methods, chosen from the oral route, the intraperitoneal route, the parenteral route or the intravenous or topical or rectal route.

Advantageously, the farnesyl transferase inhibitor constituents of the combinations according to the invention are preferably administrable by the oral route; most preferably, the farnesyl transferase inhibitor constituents of the combinations according to the invention are bioavailable by the oral route.

Advantageously, the topoisomerase inhibitor and the taxoid constituents of the combinations according to the invention are preferably administrable by the intravenous route or by the oral route in the case of irinotecan.

The products for intravenous injection are generally pharmaceutically acceptable sterile solutions or suspensions which can optionally be prepared extemporaneously at the time of use. For the preparation of non-aqueous solutions or suspensions, natural vegetable oils can be used such as olive oil, sesame oil or paraffin oil or injectable organic esters such as ethyl oleate. The sterile aqueous solutions can be formed of a solution of the product in water. The aqueous solutions are suitable for intravenous administration inasmuch as the pH is suitably adjusted and the isotonicity is produced, for example, by a sufficient quantity of sodium chloride or of glucose. Sterilization can be carried out by heating or by any other means which does not adversely affect the composition. The combinations can also be present in the form of liposomes or in combination form with supports such as cyclodextrins or polyethylene glycols.

With respect to the administration of taxoids, details are presented in U.S. Pat. Nos. 5,403,858, 5,714,512, and 5,698,582, the disclosures of which are specifically incorporated by reference herein.

As solid compositions for oral administration, compressed tablets, pills, powders (gelatin capsules, cachets) or granules can be used. In these compositions, the active principle according to the invention is mixed with one or more inert diluents, such as starch, cellulose, sucrose, lactose or silica, under a current of argon. These compositions can likewise comprise substances other than the diluents, for example one or more lubricants such as magnesium stearate or talc, a colorant, a coating (coated tablets) or a lacquer.

As liquid compositions for oral administration, it is possible to use pharmaceutically acceptable solutions, suspensions, emulsions, sirups and elixirs comprising inert diluents such as water, ethanol, glycerol, vegetable oils or paraffin oil. These compositions can comprise substances other than the diluents, for example wetting, sweetening, thickening, flavoring or stabilizing products.

The compositions for rectal administration are suppositories or rectal capsules which contain, apart from the active product(s), excipients such as cocoa butter, semi-synthetic glycerides or polyethylene glycols.

The compositions for topical administration can be, for example, creams, lotions, eye lotions, mouthwashes nasal drops or aerosols.

The doses depend on the effect sought, on the duration of the treatment and on the route of administration used; they are generally
  as far as the farnesyl transferase inhibitor is concerned: from 100 mg to 2000 mg per day by the oral route for an adult with unit doses ranging from 50 mg to 1000 mg of active substance.
  as far as the topoisomerase inhibitor is concerned: from 100 mg to 700 mg of active substance per day by the intravenous route for an adult.
  as far as the taxoid is concerned: the dosage can range from 100 mg to 700 mg of active substance per day by the intravenous route for an adult. In particular, the dosage for Taxotere® ranges from 1 to 2 mg/kg by the intravenous route for an adult. A preferred dosage for Taxotere® is 25 to 100 mg/m².

Generally speaking, the physician will determine the appropriate dosage as a function of the age, the weight and all the other factors individual to the subject to be treated.

The treatment can be repeated a number of times per day or per week until a stabilization, a partial or total remission or a recovery.

In the combinations according to the invention for which the administration of the constituents can be simultaneous, separated or spread out over time, it is particularly advantageous that the quantity of the farnesyl transferase inhibitor is from 10 to 90% by weight of the combination, it being possible for this content to vary as a function of the nature of the associated substance, the efficacy sought and the nature of the cancer to be treated.

The combinations according to the invention can be utilized for the treatment of diseases connected with malignant or benign cell proliferations of the cells of various tissues and/or organs, comprising the muscle, bone or connective tissues, the skin, the brain, the lungs, the sex organs, the lymphatic or renal systems, the mammary or blood cells, the liver, the digestive apparatus, the colon, the pancreas and the thyroid or adrenal glands, and including the following pathologies: psoriasis, restenosis, different types of sarcomas such as Kaposi's sarcoma, cancers of the head and of the neck, the pancreas, the colon, the lung, the ovary, the breast, the brain, the prostate, the liver, the stomach, the bladder, the kidney, the prostate or the testicles, Wilm's tumor, teratocarcinomas, cholangiocarcinoma, choriocarcinoma, melanomas, cerebral tumors such as neuroblastoma, gliomas, multiple myelomas, leukemias and lymphomas such as chronic lymphocytic leukemias, acute or chronic granulocytic lymphomas, and Hodgkin's disease.

The combinations according to the invention can particularly be useful for the treatment of cancers such as cancers of the pancreas, the colon, the lung, the ovary, the breast, the brain, the prostate, the liver, the stomach, the bladder or the testicles, and more advantageously cancer of the colon and of the pancreas, in particular of the colon.

In particular, they can have the advantage of being able to employ the constituents in doses which are clearly lower than those in which they are used alone.

The present invention likewise relates to the use of combinations comprising at least one farnesyl transferase inhibitor and at least one topoisomerase inhibitor, or at least one farnesyl transferase inhibitor and at least one taxoid derivative for the preparation of medicaments useful for the treatment of the abovementioned pathologies; cancers in particular.

Especially, the present invention relates to the use of combinations comprising at least one farnesyl transferase inhibitor and at least one topoisomerase inhibitor, or at least one farnesyl transferase inhibitor and at least one taxoid derivative for the preparation of medicaments for administration which is simultaneous, separate or sequenced over time.

In the present invention, the farnesyl transferase inhibitors can be made by methods known in the art, and in particular, by the methods disclosed in Ser. No. 08/999,408, now U.S. Pat. No. 6,013,662 already incorporated by reference herein. Ser. No. 08/999,408, now U.S. Pat. No. 6,013,662 refers to a process utilizing an enzyme, preferably Lipase L2 (Chirazyme®, commercialized by Boehringer Mannheim), for separating optical isomers from intermediate racemates.

Broadly, that process can be carried out on a racemic mixture of formula (X), referenced in Ser. No. 08/999,408, now U.S. Pat. No. 6,013,662 in an organic solution, such as cyclohexane, and in an aqueous solution of dipotassium hydrogenophosphate preferably adjusted to a pH ranging from 6 to 8. For example, the pH can be adjusted by adding phosphoric acid to the racemic mixture (X). Preferably, to the racemic mixture, an aqueous solution of the appropriate enzyme is added. Generally the concentration of the starting racemic mixture (X) for this particular process ranges from 5 to 50 g/l.

Preferably, the volume of the organic solution ranges form 10 to 30% volume percent relative to the total volume of the aqueous solution. Preferably, the quantity of enzyme added to the racemic mixture (X) ranges from 0.4 to 4 MU/l (1 MU is a unit of enzymatic activity).

Generally, the reaction of racemic mixture (X) with the appropriate enzyme is carried out with mixing at a temperature ranging from 20 to 40° C. The progress of the reaction can be monitored by chiral HPLC. The organic phase can be separated from the aqueous phase and additonal separation of any remaining aqueous phase can be accomplished by using an appropriate solvent or mixture of solvents, such as aliphatic alcohols, such as ethanol.

The preferred Candida Antartica "fraction B", such as the Chirazyme®, commercialized by Boehringer Mannheim, can be used to carry out the reaction leading to the desired optical isomers of (X') as disclosed in Ser. No. 08/999,408 and particularly the dextrorotatory isomers of compounds of formula (I).

The taxoids referenced herein can be prepared by means commonly known to those skilled in the art, as shown in patents already specifically incorporated by reference herein. The topoisomerase inhibitors can also be prepared by means well-known in the art.

The present invention is further illustrated by the following examples which are designed to teach those of ordinary skill in the art how to practice the invention. The following examples are merely illustrative of the invention and should not be construed as limiting the invention as claimed.

EXAMPLES

The efficacy of the combinations on solid tumors can be determined experimentally in the following manner:

The animals subjected to the experiment, generally mice, are grafted bilaterally by the subcutaneous route with 30 to 60 mg of a tumor fragment on day 0. In the case of treatment of advanced tumors, the tumors are allowed to develop to the desired size, the animals having insufficiently developed tumors being eliminated. The selected animals are divided as a function of their tumor weight in a homogeneous manner between the treated and control groups, before the start of the treatments. Chemotherapy generally commences 12 to 14 days after the implantation of the tumor and the animals are observed every day. The different groups of animals are weighed every day until the maximum loss of weight is reached and then the groups are weighed at least once per week until the end of the test. The tumors are measured 2 to 3 times per week, with the aid of a slide calliper, according to two measurements in mm which are then converted into tumor weight according to the following formula:

Tumor weight (mg)=

$$\text{Tumor weight (mg)} = \frac{\text{Length (mm)} \times \text{breadth}^2 \text{ (mm}^2\text{)}}{2}$$

The tumors are measured two or three times per week until the tumor reaches approximately 2 g or until the death of the animal if this occurs before the tumor reaches 2 g. An autopsy is carried out on the animals at the time of sacrifice.

The antitumor activity is determined as a function of the different parameters recorded.

For the study of the combinations on leukemias, the animals are grafted with a determined number of cells and the antitumor activity is determined by the increase in the time of survival of the treated mice with respect to the controls. A product is considered as active if the time of increase of survival is greater than 27% and it is considered as very active if it is greater than 75% in the case of P388 leukemia.

By way of examples, the following tables give the results obtained with combinations of the following farnesyl transferase inhibitor:

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid (dextrorotatory enantiomer), called product "A" below, with the toposiomerase inhibitors irinotecan and/or camptothecin.

TABLE 1

Activity of the combination A + irinotecan on the colon tumor HCT116 grafted by the subcutaneous route onto female nu/nu Swiss mice
Time of doubling of the tumor = 3.4 days
Size of the tumor at the start of the treatments = 75–260 mg, with a median tumor weight per group of 148–158 mg.
Length of treatment: A = 12 days, irinotecan = 9 days, A + irinotecan = 23 days.

| Product | Dose mg/kg per injection | Administration on days | (T-C)- (Duration of treatment) | net log$_{10}$ of killed cells | Long-term survivors on day 154 |
|---|---|---|---|---|---|
| A | 645 | 14–25 (2x/d.) | −2.7 | −0.2 | 0/6 |
|  | 400 |  | −4.2 | −0.4 | 0/6 |
|  | 248 |  | −10.9 | −1.0 | 0/6 |
| Irinotecan + A | 64 | 14 18, 22 (2x/d.) | toxic | — | — |
|  | 41 |  | 32.5 | 2.9 | 0/5 |
|  | 25 |  | 35.9 | 3.2 | 1/5 |
|  | 15 |  | 17.3 | 1.5 | 0/5 |
| Irinotecan | 41 645 | 14, 18, 22 (2x/d.) | 38.6 | 3.4 | 4/8 |
|  | 41 400 | 25–36 (2x/d.) | 55.9 | 5.0 | 4/7 |
|  | 41 248 |  | 36.8 | 3.3 | 4/8 |
|  | 25 645 |  | 40.2 | 3.6 | 3/8 |
|  | 25 400 |  | 37.5 | 3.3 | 2/7 |
|  | 25 248 |  | 19.1 | 1.7 | 1/6 |

TABLE 2

Activity of the combination A + irinotecan on the human colon tumor HCT116 grafted by the subcutaneous route onto female nu/nu Swiss mice.
Time of doubling of the tumor = 4.5 days
Size of the tumor at the start of the treatments = 104–208 mg, with a median tumor weight per group of 150 mg.
Length of treatment: A = 12 days, irinotecan = 9 days, A + irinotecan = 23 days.

| Product | Dose mg/kg per injection | Administration on days | (T-C)- (Duration of treatment) | net log$_{10}$ of killed cells | Long-term survivors on day 154 |
|---|---|---|---|---|---|
| A | 645 | 14–25 (2x/d.) | 6.9 | 0.5 | 0/5 |
| Irinotecan | 86.0 | 14, 18, 22 (2x/d.) | toxic | — | — |
|  | 52.0 |  | 19.5 | 1.3 | 0/5 |
|  | 31.2 |  | 15.2 | 1.0 | 0/5 |
|  | 18.7 |  | 15.9 | 1.1 | 0/5 |
|  | 11.2 |  | 8.3 | 0.6 | 0.5 |
| Irinotecan + A | 52 645 |  | 43.1 | 2.9 | 1/6 |
|  | 31.2 645 | 14, 18, 22 (2x/d.) 25–36 (2x/d.) | 20.6 | 1.4 | 0/6 |
|  | 18.7 645 |  | 23.1 | 1.5 | 1/6 |
|  | 11.2 645 |  | 11.8 | 0.8 | 0/6 |

The efficacy of the combinations on the tumors can likewise be determined experimentally in the following manner: The efficacy of the combination product A/camptothecin is tested sequentially, on a cell line:

An HCT-116 cell line of human colon carcinoma (supplied by ATCC) is cultured as a monolayer in a culture medium, Dulbecco's modified Eagle, containing 2 mM L-glutamine, 2 U/ml of penicillin, 200 µg of streptomycin supplemented by 10% by volume of heat-inactivated fetal calf serum. The cells in exponential growth are trypsinized, washed with PBS and diluted to a final concentration of 20,000 cells/ml in a complete culture medium. The cells are distributed into 25 cm$^2$ culture flasks (10 ml/flask) and 6 hours after inoculating the compound to be tested (camptothecin at final concentrations of 0.001, 0.01, 0.1 µg/ml) or an equivalent volume of solvent is added. The treated or nontreated HCT-116 cells are incubated at 37° C. under a CO$_2$ atmosphere for 24 hours, then the medium is removed and the cells are washed with PBS and trypsinized. The number of viable cells is counted by the Trypan Blue exclusion method and the cells are diluted in complete culture medium to a final concentration of 60,000 cells per ml.

For each of the culture flasks which are pre-treated (nontreated, control solvent or treated with camptothecin), the cells are inoculated onto a 96-well microculture plate at a rate of 60,000 cells/ml (0.2 ml/well) in the presence of the product A at different concentrations: 3, 1, 0.3, 0.1, 0.03 and 0.01 µg/ml (each in quadruplicate) and then cultured for 72 hours. 16 hours before the end of the treatment, 0.04% Neutral Red is added to each well. At the end of the treatment, the cells are washed and lysed with 1% SDS. The incorporation of the colorant which reflects the cell growth and the viability is evaluated by measurement of the optical density at 540 nm with a multi-well spectrophotometer. The percentage of inhibition of growth is calculated from the optical density obtained for the non-treated wells resulting from nontreated HCT-116 cells.

An activity of the combination product A/camptothecin which is higher than the respective activities of each of its constituents is demonstrated.

The following example illustrates a combination according to the invention.

Suspensions of 5 to 80 mg/ml of product A in water containing 0.5% of methylcellulose and 0.5% of polysorbate 80 are prepared according to the customary technique for oral administration.

5 ml ampoules containing 250 mg of irinotecan diluted for use in water containing 5% of glucose are prepared according to the customary technique for intravenous administration.

In the groups receiving the combination of the two products, these compositions are administered separately; preferentially, the irinotecan is administered twice per day at an interval of 3 days and then, 3 days later, the product A is administered twice per day for 12 consecutive days.

The foregoing written description relates to various embodiments of the present invention. Numerous changes and modifications may be made therein without departing from the spirit and scope of the invention as defined in the following claims.

What is claimed is:

1. A composition comprising at least one topoisomerase I inhibitor and at least one farnesyl transferase inhibitor selected from the compounds of formula (I):

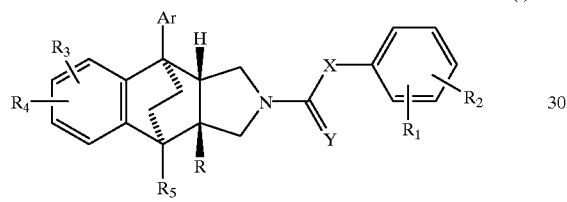

(I)

in which:

Ar is
   a phenyl radical substituted by one or more identical or different atoms or radicals, selected from halogen atoms and alkyl radicals containing 1 to 4 carbon atoms, alkenyl radicals containing 2 to 4 carbon atoms, hydroxyl, mercapto, alkylthio, alkylsulfonyl and alkylsulfinyl, amino, alkylamino and dialkylamino, formyl, alkylcarbonyl, carboxyl, alkoxycarbonyl, carbamoyl, alkylcarbamoyl and dialkylcarbamoyl, cyano and trifluoromethyl radicals, and alkoxy radicals containing 1 to 4 carbon atoms, whose alkyl portion is optionally perhalogenated;
   a phenyl radical fused to a heterocycle of 4 to 7 members containing one or more heteroatoms selected from oxygen, nitrogen and sulfur atoms;
   a polycyclic aromatic radical; or
   a heterocyclic aromatic radical of 5 to 12 chain members incorporating one or more heteroatoms selected from oxygen, nitrogen and sulfur atoms, linked to the fused ring by a carbon-carbon bond, said radical being optionally substituted, by one or more identical or different atoms or radicals, selected from halogen atoms and alkyl and alkenyl radicals containing 2 to 4 carbon atoms, hydroxyl, alkoxy radicals containing 1 to 4 carbon atoms, mercapto, alkylthio, alkylsulfonyl and alkylsulfinyl, amino, alkylamino and dialkylamino, formyl, alkylcarbonyl, carboxyl, alkoxycarbonyl, carbamoyl, alkylcarbamoyl and dialkylcarbamoyl, cyano and trifluoromethyl radicals;

R is
a radical of formula

—(CH$_2$)$_m$—X$_1$—(CH$_2$)$_n$—Z in which
   X$_1$ is a single bond or an oxygen or sulfur atom,
   m is a whole number equal to 0 or 1,
   n is a whole number equal to 0, 1 or 2,
   or one or more methylene radicals which are optionally substituted by a carboxyl, alkoxycarbonyl, carbamoyl, alkylcarbamoyl, dialkylcarbamoyl, amino, alkylamino or dialkylamino radical,
Z is
a carboxyl radical;
a COOR$_6$ radical, in which R$_6$ is a linear alkyl radical containing 1 to 3 carbon atoms, or a branched alkyl radical containing 3 carbon atoms; or
a radical of formula CON(R$_7$)(R$_8$) in which
   R$_7$ is a hydrogen atom or a linear alkyl radical containing 1 to 6 carbon atoms or a branched alkyl radical containg 3 to 6 carbon atoms; and
   R$_8$ is
      a hydrogen atom;
      a hydroxyl radical;
      an arylsulfonyl radical, optionally substituted by one or more identical or different atoms or radicals, selected from halogen atoms and alkyl and alkoxy radicals;
      a heterocycle of 5 to 7 members incorporating one or more heteroatoms selected from nitrogen, oxygen and sulfur atoms, wherein said heterocycle can be linked by a heteroatom;
      an amino radical optionally substituted by one or two identical or different radicals selected from the radicals
         alkyl containing 1 to 4 carbon atoms,
         aryl, optionally substituted by one or more identical or different radicals, selected from alkyl and alkoxy radicals, wherein said alkyl radicals contain 1 to 4 carbon atoms,
         heterocyclyl of 5 to 7 chain members and containing one or more heteroatoms selected from nitrogen, oxygen and sulfur atoms, and
         arylcarbonyl, optionally substituted by one or more identical or different radicals, selected from alkyl and alkoxy radicals, wherein said alkyl radicals contain 1 to 4 carbon atoms;
      an alkoxy radical containing 1 to 6 carbon atoms in a linear or branched chain optionally substituted by a phenyl radical; or
      a linear alkyl radical containing 1 to 6 carbon atoms or a branched alkyl radical containing 3 to 6 carbon atoms, each of said radicals being optionally substituted by an amino, alkylamino, dialkylamino or hydroxyl radical, an alkoxy radical containing 1 to 4 carbon atoms, a mercapto, alkylthio, alkoxycarbonyl, carboxyl, cyano, a mono- or polycyclic aromatic radical having 5 to 12 chain members, incorporating or not incorporating one or more heteroatoms selected from oxygen, nitrogen and optionally substituted sulfur atoms, or a phenyl radical optionally substituted by one or more halogen atoms or by one or more hydroxyl, amino ortrifluoromethyl groups, or by one or more C2 to C4 alkyl or alkenyl, alkoxy, alkylthio, alkylamino, alkylcarbonyl or alkoxycarbonyl radicals, a carbamoyl, alkylcarbamoyl or dialkylcarbamoyl whose alkyl part is C1 to C8, formyl or a 1- or 2-naphthyl radical; or Z is a PO(OR$_9$)$_2$ radical in which R$_9$ is a hydrogen atom or a linear alkyl radical containing 1 to 6 carbon atoms or a branched alkyl radical containing 3 to 6 carbon atoms, or an —NH—CO—T radical in which T is a hydrogen atom or a linear alkyl radical containing 1 to 6 carbon atoms or a branched alkyl radical containing 3 to 6 carbon atoms, each of said radicals being optionally substituted by an amino, carboxyl, alkoxycarbonyl, hydroxyl, alkoxy, mercapto or alkylthio radical, or

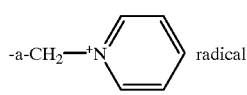 radical having, as counterion, an anion;

R$_1$ and R$_2$, which are identical or different, are a hydrogen atom, a halogen or an alkyl radical, an alkoxy radical, each optionally substituted by a dialkylamino radical of which each alkyl part contains 1 to 4 carbon atoms or forms, with the nitrogen atom, a saturated heterocycle containing 5 or 6 chain members, an alkylthio radical, an alkoxycarbonyl radical, or when situated ortho with respect to one another, R$_1$ and R$_2$ may form a saturated or unsaturated heterocycle containing 1 or 2 heteroatoms selected from nitrogen and oxygen, optionally substituted by a halogen atom or by an alkyl or alkoxy radical;

R$_3$ and R$_4$, which are identical or different, are a hydrogen or halogen atom or an alkyl, hydroxyl, alkoxy, alkylcarbonyloxy, mercapto, alkylthio, alkylsulfonyl or alkylsulfinyl, amino, alkylamino or dialkylamino, alkoxycarbonylamino, carboxyl, alkoxycarbonyl, carbamoyl, alkylcarbamoyl or dialkylcarbamoyl, formyl, alkylcarbonyl, cyano or trifluoromethyl radical;

R$_5$ is a hydrogen atom or an alkyl radical, or an alkylthio radical;

X is an oxygen or sulfur atom or an —NH—, —CO—, methylene, or alkene-1-diyl group; and Y is an oxygen or sulfur atom;

in a racemic form, in the form of an optical isomer or in the form of a salt thereof.

2. A composition as claimed in claim 1, wherein said at least one farnesyl transferase inhibitor is chosen from the compounds of general formula (I) for which:

Ar is a 2,3-dihydro-1,4-benzodioxin-6-yl or 2,3-dihydrobenzofuran-5-yl radical, or a substituted phenyl radical, R is a carboxyl radical, or a —COOMe radical, or a —CON(R$_7$)(R$_8$) radical for which when R$_7$ is a hydrogen atom, R$_8$ is a methyl radical substituted by a 3-pyridyl radical, one of the symbols R$_1$ or R$_2$ is a hydrogen atom and the other of the symbols is a methoxy radical, R$_3$ and R$_4$ each represent a hydrogen atom, or one of the symbols R$_3$ or R$_4$ is a hydrogen atom and the other of the symbols R$_3$ or R$_4$ is a methoxy radical, R$_5$ is a hydrogen atom or a methyl radical, X is a methylene or vinyidiyl group, Y is an oxygen atom;

in a racemic form, in the form of an optical isomer or in the form of a salt thereof.

3. A composition as claimed in claim 1, wherein X is a vinyidiyl or cycloalkane-1,1-diyl containing 3 to 6 carbon atoms.

4. A composition as claimed in claim 1, wherein said at least one farnesyl transferase inhibitor is selected from the compounds:

(3aRS, 4SR,9SR,9aRS)-4,9-ethano-2(2-(2-methoxyphenyl)propenoyl) -9-(4-methylphenyl)-2,3,3a,4,9,9a-hexahydro-1H-benzo(f)isoindole-3a-carboxylic acid;

(3aRS,4SR,9SR,9aRS)-4,9-ethano-2(2-(2-methoxyphenyl)-propenoyl)-9-(4-methylphenyl)-2,3,3a,4,9,9a-hexahydro-1H-benzo(f)isoindole-3a-N-(3-pyridylmethyl)carboxamide;

(3aRS,4SR,9SR,9aRS)-9-(2,3-dihydro-1,4-benzodioxin-6-yl)-4,9-ethano-2-(2-(2-methoxyphenyl)propenoyl)-2,3,3a,4,9,9a-hexahydro-1H-benzo(f)isoindole-3a-N-(3-pyridylmethyl)carboxamide;

(3aRS,4SR,9SR,9aRS)-4,9-ethano-2-(2-(2-methoxyphenyl)propenoyl)9-(4-trifluoromethylphenyl)-2,3,3a,4,9,9a-hexahydro-1H-benzo(f)isoindole-3a-carboxylic acid;

(3aRS,4SR,9SR,9aRS)-9-(2,3-dihydrobenzofuran-5-yl)-4,9-ethano-2-(2-(2-methoxyphenyl)propenoyl)-2,3,3a,4,9,9a-hexahydro-1H-benzo(f)isoindole-3a-N-(3-pyridylmethyl)carboxamide;

(3aRS,4SR,9SR,9aRS)-4,9-ethano-9-(4-methoxyphenyl)-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)-4,9-ethano-5-methoxy-2-(2-(2-methoxyphenyl)-propenoyl-9-(4-methylphenyl)-2,3,3a,4,9,9a-hexahydro-1H-benzo(f)isoindole-3a-carboxylic acid; and (3aRS,4SR,9SR,9aRS)-4,9-ethano-2(2-(2-methoxyphenyl)-2-propenoyl)-4-methyl-9-(4-methoxyphenyl)-2,3,3a,9,9a-hexahydro-1H-benzo(f)isoindole-3a-carboxylic acid;

in a racemic form, in the form of an optical isomer or in the form of a salt thereof.

5. A composition as claimed in claim 4, wherein said at least one farnesyl transferase inhibitor is the dextrorotatory enantiomer of (3aRS,4SR,9SR,9aRS) 4,9-ethano-2[2-(2-methoxyphenyl)propenoyl]-9-(4-methylphenyl)-2,3,3a,4,9,9a-hexahydro-1H-benzo[f] isoindole-3a-carboxylic acid.

6. A composition as claimed in claim 1, wherein said at least one topoisomerase I inhibitor is irinotecan.

7. A composition comprising the dextrorotatory enantiomer of (3aRS,4SR,9SR,9aRS)-4,9-ethano-2[2-(2-methoxyphenyl)propenoyl]-9-(4-methylphenyl)-2,3,3a,4,9,9a-hexahydro-1H-benzo[f]isoindole-3a-carboxylic acid and irinotecan.

8. A composition comprising the dextrorotatory enantiomer of (3aRS,4SR,9SR,9aRS)-4,9-ethano-2[2-(2-methoxyphenyl)propenoyl]-9-(4-methylphenyl)-2,3,3a,4,9,9a-hexahydro-1H-benzo[f]isoindole-3a-carboxylic acid and camptothecin.

9. A method of treating cancer comprising administering to a patient in need thereof a pharmaceutical composition comprising an effective amount of at least one farnesyl transferase inhibitor and at least one topoisomerase inhibitor according to claim 1.

10. The method of claim 9, wherein said at least one farnesyl transferase inhibitor and at least one topoisomerase inhibitor are administered simultaneously, separately, or sequenced over time.

11. A composition according to claim 1, wherein in said Ar, said perhalogenated alkyl portion is trifluoromethoxy; wherein said $R_6$ is methyl; and wherein said anion is trifluoromethanesulfonate.

* * * * *